US006855118B2

(12) United States Patent
Linton

(10) Patent No.: US 6,855,118 B2
(45) Date of Patent: Feb. 15, 2005

(54) METHOD AND APPARATUS FOR MEASURING LEG LENGTH IN AN UPRIGHT POSITION

(76) Inventor: LoRal G. Linton, 662 S. Highway 89-A, Kanab, UT (US) 84741

( * ) Notice: Subject to any disclaimer, the term of this patent is extended or adjusted under 35 U.S.C. 154(b) by 234 days.

(21) Appl. No.: 10/229,994

(22) Filed: Aug. 28, 2002

(65) Prior Publication Data

US 2004/0044296 A1 Mar. 4, 2004

(51) Int. Cl.⁷ .............................................. A61B 5/103
(52) U.S. Cl. ......................................... 600/587; 33/511
(58) Field of Search ................................ 600/300, 587, 600/594, 595; 33/511, 512

(56) References Cited

U.S. PATENT DOCUMENTS

| 809,836 A | * | 1/1906 | Nordstrom | 33/7 |
| 4,444,204 A | * | 4/1984 | Bryant et al. | 600/594 |
| 4,823,476 A | | 4/1989 | Curtin | |
| 4,872,268 A | * | 10/1989 | Perrault | 33/512 |
| 4,883,066 A | | 11/1989 | Widdoes et al. | |
| 5,060,393 A | | 10/1991 | Silverman et al. | |
| 5,156,162 A | * | 10/1992 | Gerhardt | 600/594 |
| 5,814,050 A | | 9/1998 | Benson | |
| 5,823,974 A | * | 10/1998 | Grassi | 600/595 |
| 5,966,827 A | * | 10/1999 | Horvath et al. | 33/512 |
| 6,565,519 B2 | * | 5/2003 | Benesh | 600/587 |

OTHER PUBLICATIONS

*Textbook of Orthopedic Medicine*, James Cyriax, p. 104.
*Low Back Pain*, James Cox, Williams & Wilkins, pp. 118–119.
*Physical Examination of the Spine and Extremities*, Stanley Hoppenfeld, p. 166.

* cited by examiner

Primary Examiner—Charles Marmor
(74) Attorney, Agent, or Firm—Thorpe North & Western, LLP

(57) ABSTRACT

An apparatus for measuring body symmetry is disclosed. The apparatus includes a pair of supports, a level, and means for determining support displacement. The supports position the apparatus on left and right body points that are generally symmetrical about a patient's spinal column. The level indicates whether the first support is higher or lower than the second support when placed upon the left and right body points thereby identifying that the body points are not actually symmetrical. The means for determining support displacement determine the displacement of one support relative to the other in a vertical direction when one body point is higher or lower than the other body point. The apparatus is utilized to determine hip or shoulder symmetry and displacement.

4 Claims, 2 Drawing Sheets

METHOD AND APPARATUS FOR MEASURING LEG LENGTH IN AN UPRIGHT POSITION

BACKGROUND OF THE INVENTION

The present invention relates generally to a measuring device for measuring anatomical features of a patient and, more specifically, the present invention relates to measuring a patient's hip, leg, or shoulder tilt with respect to one side versus the other to determine proper alignment and length, among others.

The human body has a symmetry that requires that each limb and the skeletal structure remain in proper alignment and substantially level as compared one side to the other. This symmetry leads to proper health and wellbeing. When dissymmetry occurs, such as when one limb is shorter than the other one, for example one leg being shorter than the other leg, poor health, pain and improper spinal curvatures as scoliosis can result. This dissymmetry also occurs when the hips through the pelvis are not level from side to side or when the shoulders are not level from side to side. In one study it was found that 11 percent of patients experiencing lower back pain were found to have a leg length discrepancy.

In order to identify the cause of this dissymmetry, different methods may be used. For example, one determines whether one leg is the same length as the other or whether the pelvis is properly horizontal, which in each case may be accomplished by taking measurements of the patient's body. In one method, the patient stands upright with the feet generally parallel to one another, slightly spaced apart, and the level of the iliac crests of the hips is determined. Boards are placed under the foot of the shorter limb until the pelvis of the patient becomes horizontal. If the lumbar tilt ceases when the iliac crests are rendered level, it is the result of one leg being shorter than the other.

If the patient experiences discomfort while standing, or on lumbar flexion or extension, the patient's shorter leg is raised by a platform under the patient's foot. If this eases or abolishes the patient's pain, the patient is then recommended to wear a raised heel indefinitely.

One problem with having the patient stand and then placing boards under the patient's foot is that it is still difficult to determine when the patient's pelvis becomes horizontal. This becomes a subjective observation by the individual conducting the exam and may not always accurately determine the amount of displacement that exists from one limb being shorter than the other limb or from the pelvis tilt or lumbar tilt leveling out.

Another way to measure whether one limb is longer than the other is to measure the length of each limb relative to a central point of the body. Thus, an examiner measures from a non-fixed point to a fixed point to determine the apparent leg length discrepancy. In this case, the fixed point usually is the patient's navel and the non-fixed point is either the patient's heel or ankle.

When measuring from the fixed point, this may determine whether the leg is shorter than the other, but the actual cause of the leg being shorter than the other may be because of a pelvic obliquity, meaning that the pelvic bone is unlevel and not horizontal. Accordingly, both legs may have the same length as measured with respect to the iliac crest, but this would not be determined by using the fixed point or navel of the patient. Further, it is difficult to determine how much tilt exists across the iliac crest using conventional means.

X-ray incorporating the full pelvis and lower extremities may also be taken and then measured. X-rays subject the patient to radiation exposure as well as to the inconvenience of visiting the radiology center and undergoing the radiological procedure.

Accordingly, there is a need for an apparatus and method for measuring the proper length of a patient's limb, such as a leg, that factors in the lumbar tilt without including false measurements typically caused by subjective observations utilized in the prior art.

SUMMARY OF THE INVENTION

According to the invention, an apparatus for measuring body symmetry is disclosed. The apparatus includes a pair of supports, a level, and means for determining support displacement. The supports position the apparatus on left and right body points that are generally symmetrical about a patient's spinal column. The level indicates whether the first support is higher or lower than the second support when placed upon the left and right body points thereby identifying that the body points are not actually symmetrical. The means for determining support displacement determine the displacement of one support relative to the other in a vertical direction when one body point is higher or lower than the other body point. In one embodiment, the level comprises a first level indicator mounted to one of the pair of supports and a second level indicator mounted to the other of the pair of supports such that both level indicators register a common value when placed in the same horizontal plane and vertically parallel to each other. The first level indicator and the second level indicator share a common tube filled with fluid to indicate levelness.

A horizontal level indicator can be placed on a top portion of the apparatus generally between the first and second supports. The supports are horizontally adjustable between body points for accurate placement on different patients or different body points of the same patient.

In one embodiment, the apparatus is utilized to measure the inequality of limb length or hip symmetry of a patient. The pair of supports is positioned on either iliac crest of the patient. The level indicates whether the first support is higher or lower than the second support when placed upon the iliac crests. The determining means determines the displacement of one support relative to the other in a vertical direction and measures the amount of that displacement to determine the limb length inequality. The apparatus may be utilized on other body parts to determine tilt, such as, for example, the shoulder and head.

The level comprises a first level indicator mounted to one of the pair of supports and a second level indicator mounted to the other of the pair of supports such that both level indicators register a common value when placed in the same horizontal plane and vertically parallel to each other so as to show the actual length of misalignment.

Additional features and advantages of the invention will be apparent from the detailed description which follows, taken in conjunction with the accompanying drawings, which together illustrate, by way of example, features of the invention.

DETAILED DESCRIPTION OF SPECIFIC EMBODIMENTS

Figure 2:
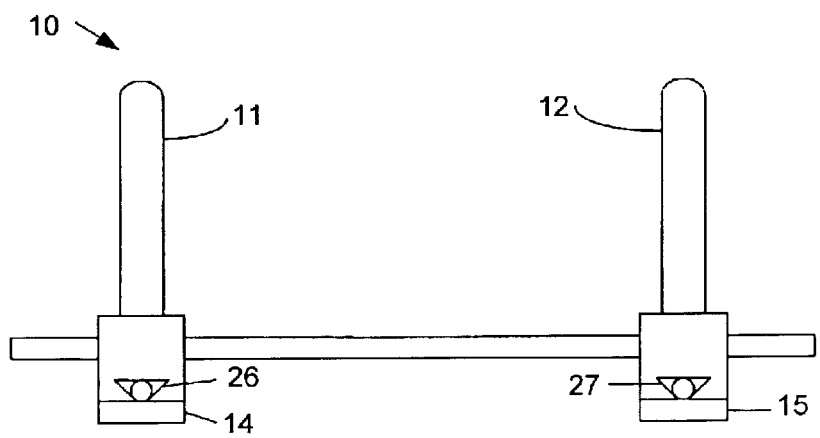
FIG. 2 illustrates a back view of the apparatus as embodied in FIG. 1.
Figure 1:
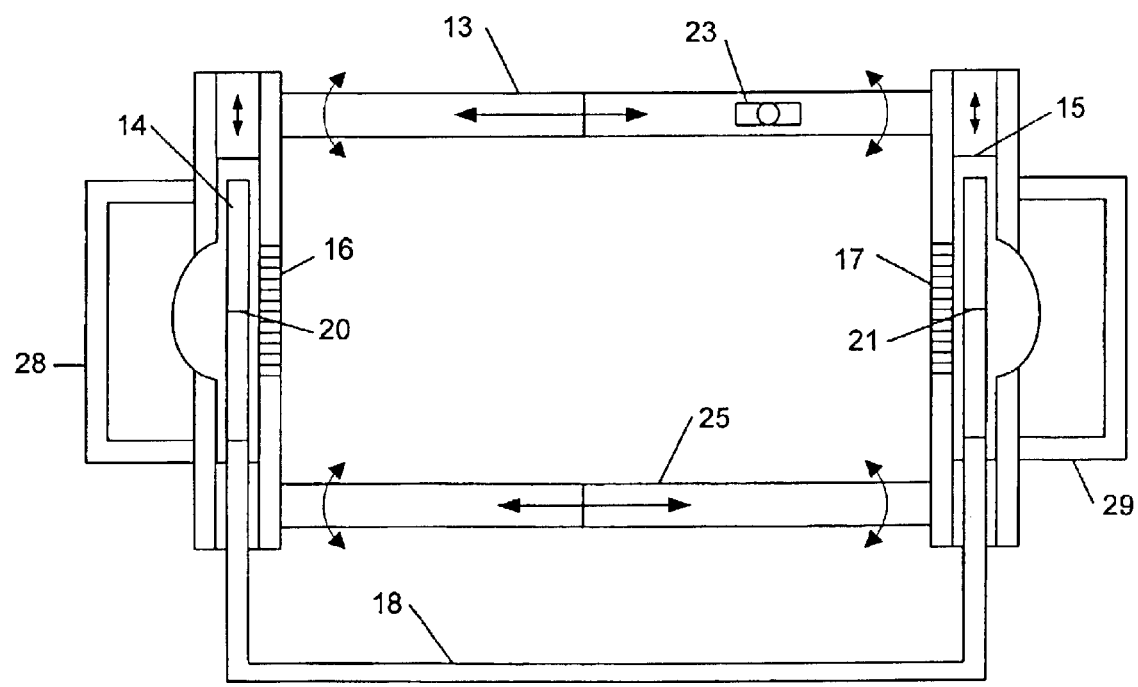
FIG. 1 illustrates a top view of an apparatus for measuring a patient's leg length and levelness of the patient's pelvis in accordance with the present invention.
Figure 3:
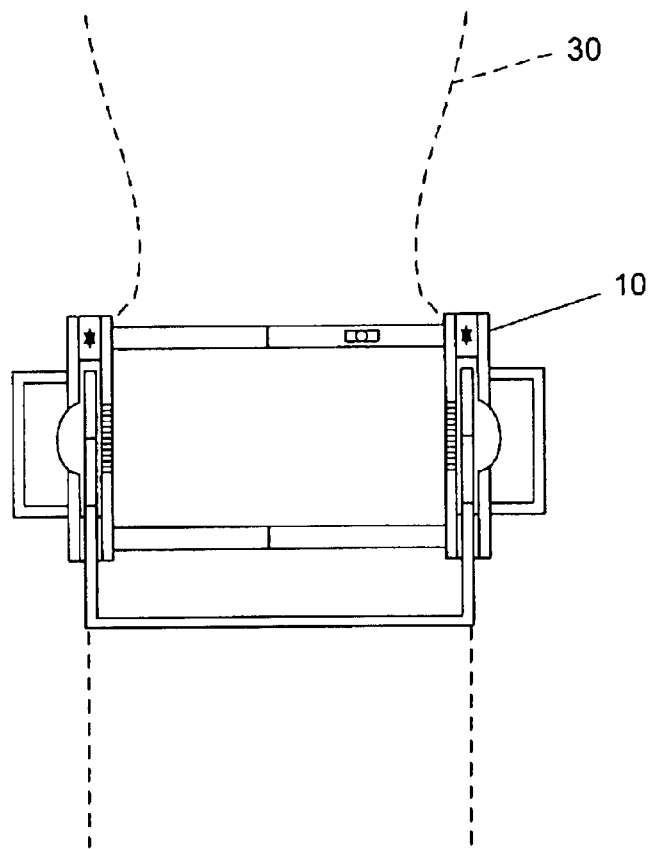
FIG. 3 illustrates a front view of one embodiment of the invention as positioned on the hips of a patient.

For the purposes of promoting an understanding of the principles of the invention, reference will now be made to the exemplary embodiments illustrated in the drawings, and specific language will be used to describe the same. It will nevertheless be understood that no limitation of the scope of the invention is thereby intended. Any alterations and further modifications of the inventive features illustrated herein, and any additional applications of the principles of the invention as illustrated herein, which would occur to one skilled in the relevant art and having possession of this disclosure, are to be considered within the scope of the invention.

An apparatus for measuring the leg length of a patient to determine leg length inequality or to determine whether the patient's pelvis is out of horizontal alignment is shown in FIGS. 1–4 as measuring apparatus 10. Apparatus 10 includes a first support 11 and a second support 12 that are substantially identical and serve to position apparatus 10 on generally symmetrically horizontal body points about the patient's spine, such as on top of a patient's iliac crests on either side of the pelvis or across the shoulders of the patient, among others. A cross-support 13 that allows for both supports 11 and 12 to be positioned to rest on the proper crest point of the patient's pelvis is also provided. Cross-support 13 can slide in and out in a tensioned manner by friction, screws or spring force.

Each side of apparatus 10 includes a first level indicator 14 and a second level indicator 15. Each level indicator 14 and 15 includes measurement indicators 16 and 17, respectively. The measurement indicators 16 and 17 can provide a positive or negative reading with respect to horizontal. Both level indicators 14 and 15 are coupled together with a fluid filled flexible tube 18. Tube 18 holds sufficient fluid such that when apparatus 10 is in a completely horizontal position, the fluid registers at the zero-difference measurement level on measurement indicators 16 and 17. Sight glasses 20 and 21 are provided for each level 14 and 15, respectively, to show the position of the fluid within tube 18. As apparatus 10 is out of horizontal alignment, the fluid indicates what level of vertical displacement has occurred by way of the measurement indicators 16 and 17. For example, if the pelvic tilt is 2 cm, then a first level indicator 16 may be at plus or minus (+/−) 1 cm while the other level indicator 15 would be at −/+1 cm.

A leveling device 23 is placed in a horizontal position on cross-support 13. Leveling device 23 typically includes a fluid that has a level bubble therein and the bubble moves in the direction of the longer leg or the higher tilted pelvic crest.

Apparatus 10 includes a second cross-support 25 that provides greater stability than merely having a single cross-support. Both cross-supports 13 and 25 can slide in and out to accommodate the proper girth of different patients. Further, both supports 13 and 25 may rotate about a central axis to enable proper fitting on the patient's iliac crests. A pair of handles 28 and 29 is mounted on either side of apparatus 10 to enable the examiner to place and properly align apparatus 10 on the patient's iliac crests.

Figure 4:
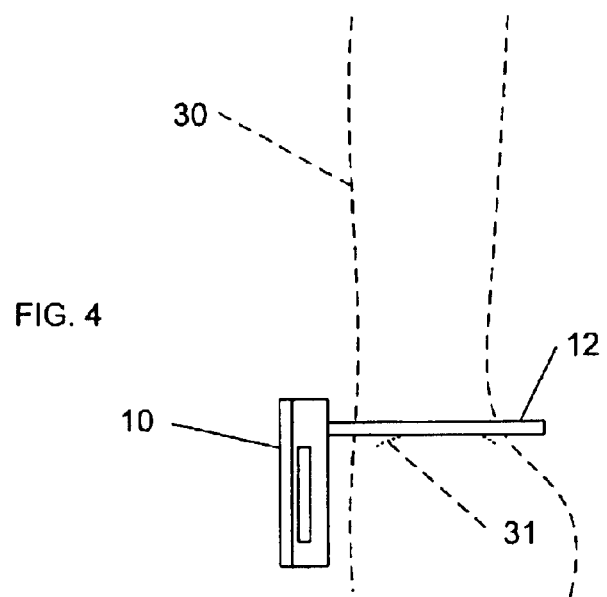
FIG. 4 illustrates a side view of the apparatus as embodied in FIG. 3.

The procedure begins by having the patient 30 stand in their bare feet on a hard level surface, place his or her feet straight and generally parallel with the feet being spaced about the same width as the hips or femoral heads and such knees are straight or fully extended. Next, the apparatus 10 is placed on top of the iliac crest 31 of the patient 30 such that supports 11 and 12 are in contact with the patient's body, as shown in FIG. 4. Once the apparatus 10 is in place on the patient's body, the examiner provides a leveling adjustment of indicators 14 and 15 and then trues the levels so that one side is at zero, thereby allowing the other side to give the true measurement. Alternatively, the measurements placed on measurement indicators 16 and 17 may be in half scale so that the examiner merely adds the two values to arrive at the proper measurement. The level 23 indicates which leg is longer or pelvic side is higher than the other leg or side.

In one embodiment, both level indicators 14 and 15 move in unison, within respective friction tracks 26 and 27, and by the same amount when so moved. Thus, as level indicator 14 moves upwards 1 cm, so too does level 15 move upwards 1 cm. If this were not the case, then a true and accurate reading of leg length inequality or iliac crest misalignment would not be achieved.

The application to measuring alignment of the shoulders, head or other symmetrical locations of the body would follow the same procedures as outlined for measuring hip alignment and leg length. The apparatus is placed across the shoulders at mutually symmetrical points that are normally aligned horizontally to each other about the patient's spine. Any measurement of misalignment will indicate the shoulders are out of alignment. Of course, the hips and other body parts will need to be ruled out as the possible source for such misalignment and can be done quickly through the use of the measuring application as embodied in the present invention.

Although the apparatus 10 utilizes levels based on a fluid material, other types of levels are also possible. Alternative levels may include using a laser reflecting system or a pendulum based measuring device may also be contemplated. The pendulum hangs perpendicularly to the ground due to the gravitational force and an angle of displacement is quickly calculated. Knowing the width of separation of the first support 11 from the second support 12, as well as the angle of deflection, a difference in height or leg length can be quickly calculated.

After determining short leg, an insert may be placed into the shoe of the size determined from the calculations from this invention. A re-check can then be done with the instrument for verification. The clinician can have the patient wear the insert, have the shoe built-up or prescribe other procedures to correct the area of inequality.

Other embodiments include using an interferometer, as well as other electromagnetic waves such as sound waves, light waves or magnet displacement. Additionally, a fluoroscope measuring means may also be included. Alternative embodiments may also utilize magnetic resonant imaging (MRI) or performing a CAT scan.

It is to be understood that the above-described arrangements are only illustrative of the application of the principles of the present invention. Numerous modifications and alternative arrangements may be devised by those skilled in the art without departing from the spirit and scope of the present invention. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An apparatus for measuring body symmetry, comprising:

a pair of supports, for positioning the apparatus on left and right body points that are generally symmetrical about a patient's spinal column;

a first level indicator, mounted to one of the pair of supports;

a second level indicator, mounted to the other of the pair of supports, configured to register a common value with the first level indicator when the pair of supports are placed in the same horizontal plane and vertically parallel to each other;

a tube, shared by the first and second level indicators, filled with fluid to indicate the relative displacement of the supports; and means for determining the displacement of one support relative to the other in a vertical direction when one body point is higher or lower than the other body point.

2. The apparatus as in claim 1 further comprising a horizontal level indicator placed on a top portion of the apparatus generally between the first and second supports.

3. The apparatus as in claim 1 wherein the supports are horizontally adjustable between body points for accurate placement on different patients or different body points of the same patient.

4. An apparatus for measuring inequality of limb length or hip symmetry of a patient, comprising:

a pair of supports for positioning the apparatus on either iliac crest of the patient;

a first level indicator, mounted to one of the pair of supports;

a second level indicator, mounted to the other of the pair of supports, configured to register a common value with the first level indicator when the pair of supports are placed in the same horizontal plane and vertically parallel to each other;

a tube, shared by the first and second level indicators, filled with fluid to indicate the relative displacement of the supports; and means for determining the displacement of one support relative to the other in a vertical direction and measuring the amount of that displacement to determine the limb length inequality.

* * * * *